US00PP20850P2

(12) United States Plant Patent
Dümmen

(10) Patent No.: US PP20,850 P2
(45) Date of Patent: Mar. 16, 2010

(54) ***PETUNIA* PLANT NAMED 'DUESURWICE'**

(50) Latin Name: *Petunia×hybrida*
Varietal Denomination: Duesurwice

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/316,476

(22) Filed: Dec. 12, 2008

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

PP17,681 P2 * 5/2007 Iwaki et a ..... Plt./356

OTHER PUBLICATIONS

UPOV ROM GTITM Computer Database, GTI Jouve Retrieval Software 2009/03 Citation for 'Duesurwice'.*

* cited by examiner

*Primary Examiner*—Wendy C Haas
(74) *Attorney, Agent, or Firm*—C. A. Whealy

(57) ABSTRACT

A new and distinct cultivar of *Petunia* plant named 'Duesurwice', characterized by its outwardly spreading to trailing growth habit; freely branching habit; early and freely flowering habit; pale pink-colored flowers with purple-colored venation; and good garden performance.

1 Drawing Sheet

Botanical designation: *Petunia×hybrida.*
Cultivar denomination: 'Duesurwice'.

CROSS-REFERENCED TO CLOSELY RELATED APPLICATIONS

U.S. Plant patent application Ser. No. 12/316,457.

BACKGROUND OF THE INVENTION

The present invention relates to a new and distinct cultivar of *Petunia* plant, botanically known as *Petunia×hybrida* and hereinafter referred to by the name 'Duesurwice'.

The new *Petunia* plant is a product of a planned breeding program conducted by the Inventor in Rheinberg, Gernany. The objective of the breeding program is to create new trailing *Petunia* cultivars with numerous attractive flowers.

The new *Petunia* plant originated from a cross-pollination made by the Inventor in August, 2005 in Rheinberg, Germany of a proprietary selection of *Petunia×hybrida* identified as code number T04-0063-008, not patented, as the female, or seed, parent with a proprietary selection of *Petunia×hybrida* identified as code number F-19-18, not patented, as the male, or pollen, parent. The new *Petunia* was discovered and selected by the Inventor as a single flowering plant within the progeny of the stated cross-pollination in a controlled greenhouse environment in Rheinberg, Germany in May, 2007.

Asexual reproduction of the new *Petunia* plant by terminal cuttings in a controlled greenhouse environment in Rheinberg, Germany since May, 2007, has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Duesurwice'. These characteristics in combination distinguish 'Duesurwice' as a new and distinct cultivar of *Petunia:*

1. Outwardly spreading to trailing growth habit.
2. Freely branching habit.
3. Early and freely flowering habit.
4. Pale pink-colored flowers with purple-colored venation.
5. Good garden performance.

Plants of the new *Petunia* can be compared to plants of the female parent selection. Plants of the new *Petunia* differ primarily from plants of the female parent selection in flower color. In addition, plants of the new *Petunia* are more vigorous than plants of the female parent selection.

Plants of the new *Petunia* can be compared to plants of the male parent selection. Plants of the new *Petunia* differ primarily from plants of the male parent selection in plants size as plants of the new *Petunia* are more compact than plants of the male parent selection. In addition, plants of the new *Petunia* have larger flowers than plants of the male parent selection.

Plants of the new *Petunia* differ primarily from plants of *Petunia×hybrida* 'Duesurimwi', disclosed in U.S. Plant patent application Ser. No. 12/316,457, in flower color as plants of 'Duesurimwi' have white-colored flowers.

Plants of the new *Petunia* can be compared to plants of the *Petunia×hybrida* 'Sunhore', disclosed in U.S. Plant Pat. No. 17,681. In side-by-side comparisons conducted in Rheinberg, Germany, plants of the new *Petunia* differed primarily from plants of 'Sunhore' in the following characteristics:

1. Plants of the new *Petunia* were more compact than plants of 'Sunhore'.
2. Plants of the new *Petunia* had narrower leaves than plants of 'Sunhore'.

3. Plants of the new *Petunia* had larger flowers with longer peduncles than plants of 'Sunhore'.
4. Plants of the new *Petunia* and 'Sunhore' differed in flower color as plants of 'Sunhore' had coral pink-colored flowers.

BRIEF DESCRIPTION OF THE PHOTOGRAPH

The accompanying colored photograph illustrates the overall appearance of the new *Petunia*, showing the colors as true as it is reasonably possible to obtain in colored reproductions of this type. Colors in the photograph may differ slightly from the color values cited in the detailed botanical description which accurately describe the colors of the new *Petunia* plant. The photograph comprises a close-up view of typical flowers and leaves of 'Duesurwice'.

DETAILED BOTANICAL DESCRIPTION

The aforementioned photograph and following observations, measurements and values describe plants grown in Rheinberg, Germany, under commercial practice during the spring in a glass-covered greenhouse with day and night temperatures averaging 18° C. and light levels averaging 4,500 lux. Rooted young plants had been growing for 16 weeks when the photograph and description were taken. Plants were pinched one time about three weeks after planting. In the following description, color references are made to The Royal Horticultural Society Colour Chart, 2001 Edition, except where general terms of ordinary dictionary significance are used.

Botanical classification: *Petunia×hybrida* 'Duesurwice'.

Parentage:

*Female, or seed, parent.*—Proprietary selection of *Petunia×hybrida* identified as code number T04-0063-008, not patented.

*Male, or pollen, parent.*—Proprietary selection of *Petunia×hybrida* identified as code number F-19-18, not patented.

Propagation:

*Type.*—By terminal cuttings.

*Time to initiate roots, summer.*—About seven days at temperatures of 20° C.

*Time to initiate roots, winter.*—About ten days at temperatures of 20° C.

*Time to produce a rooted young plant, summer.*—About three weeks at temperatures of 20° C.

*Time to produce a rooted young plant, winter.*—About four weeks at temperatures of 20° C.

*Root description.*—Fine, fibrous; white in color.

*Rooting habit.*—Freely branching; dense.

Plant description:

*Plant and growth habit.*—Outwardly spreading to trailing growth habit. Freely branching habit with about eight to ten lateral branches developing after pinching. Moderately vigorous growth habit.

*Plant height.*—About 16 cm.

*Plant diameter.*—About 25 cm.

Lateral branch description:

*Length.*—About 24 cm.

*Diameter.*—About 3 mm.

*Internode length.*—About 3.7 cm.

*Strength.*—Moderately strong.

*Aspect.*—Initially upright to outwardly spreading.

*Texture.*—Pubescent.

*Color.*—Close to 144A to 144B.

Foliage description:

*Arrangement.*—Before flowering, alternate, simple; after flowering, opposite, simple.

*Length.*—About 4.5 cm.

*Width.*—About 1.9 cm.

*Shape.*—Spatulate.

*Apex.*—Obtuse.

*Base.*—Attenuate.

*Margin.*—Entire.

*Texture, upper and lower surfaces.*—Pubescent; leathery.

*Venation pattern.*—Pinnate; arcuate.

*Color.*—Developing and fully expanded leaves, upper surface: Close to 137A; venation, close to 144B. Developing and fully expanded leaves, lower surface: Close to 137C; venation, close to 144B.

*Petiole length.*—About 5 mm.

*Petiole diameter.*—About 3 mm.

*Petiole texture, upper and lower surfaces.*—Pubescent.

*Petiole color, upper and lower surfaces.*—Close to 144B.

Flower description:

*Flower arrangement and habit.*—Salverform flowers; single flowers arising from leaf axils. Freely flowering habit with usually about 25 to 30 open flowers and flower buds per plant. Flowers face upright to outwardly.

*Fragrance.*—None detected.

*Natural flowering season.*—Plants flower continuously from late spring into autumn in Germany. Early flowering habit, plants typically beginning flowering about nine weeks after planting.

*Flower longevity.*—Individual flowers last about five days on the plant; flowers persistent.

*Flower diameter.*—About 7 cm.

*Flower length (height).*—About 3 cm.

*Flower throat diameter.*—About 1.2 cm.

*Flower tube diameter.*—About 3 mm.

*Flower bud.*—Shape: Ovoid. Length: About 4.1 cm. Diameter: About 7 mm. Color: Close to 3D; venation, close to 59A.

*Corolla.*—Arrangement: Five petals fused at the base and opening into a flared trumpet. Petal length from throat: About 2.8 cm. Petal lobe width: About 3.2 cm. Petal shape: Roughly spatulate. Petal apex: Rounded. Petal margin: Entire. Petal texture, upper and lower surfaces: Smooth, glabrous; satiny. Throat texture: Smooth, glabrous. Tube texture: Pubescent. Color: Petal, when opening, upper and lower surfaces: Close to 69D. Petal, fully opened, upper and lower surfaces: Close to 69B; color becoming closer to 69C with development; venation, close to 61A. Flower throat: Close to 60C; venation, close to 61A. Flower tube: Close to 59B; venation, close to 61A.

*Calyx.*—Arrangement: One star-shaped calyx tube with five sepals fused at the base per flower. Sepal length: About 3 cm. Sepal width: About 5 mm. Sepal shape: Narrowly oblong. Sepal apex: Rounded. Sepal margin: Entire. Sepal texture, upper and lower surfaces: Pubescent. Color, immature and mature, upper surface: Close to 137A. Color, immature and mature, lower surface: Close to 137C.

*Peduncles.*—Length: About 3.4 cm. Diameter: About 2 mm. Strength: Moderately strong. Texture: Pubescent. Color: Close to 144B.

*Reproductive organs.*—Stamens: Quantity/arrangement: Five per flower. Anther shape: Ovate. Anther length: About 2.5 mm. Anther color: Close to 2D. Pollen amount: Abundant. Pollen color: Close to 2D. Pistils: Quantity: One per flower. Pistil length: About 2 cm. Style length: About 1.9 cm. Style color:

Between 144B and 145C. Stigma shape: Rounded. Stigma color: Close to 144B. Ovary color: Close to 144B. Seed/fruit: Seed and fruit development have not been observed on plants of the new *Petunia*.

Garden performance: Plants of the new *Petunia* have been observed to have good garden performance and tolerate wind, rain and temperatures ranging from about 2° C. to about 38° C.

Pathogen/pest resistance: Plants of the new *Petunia* have not been observed to be resistant to pathogens and pests common to *Petunia*.

It is claimed:

1. A new and distinct *Petunia* plant named 'Duesurwice' as illustrated and described.

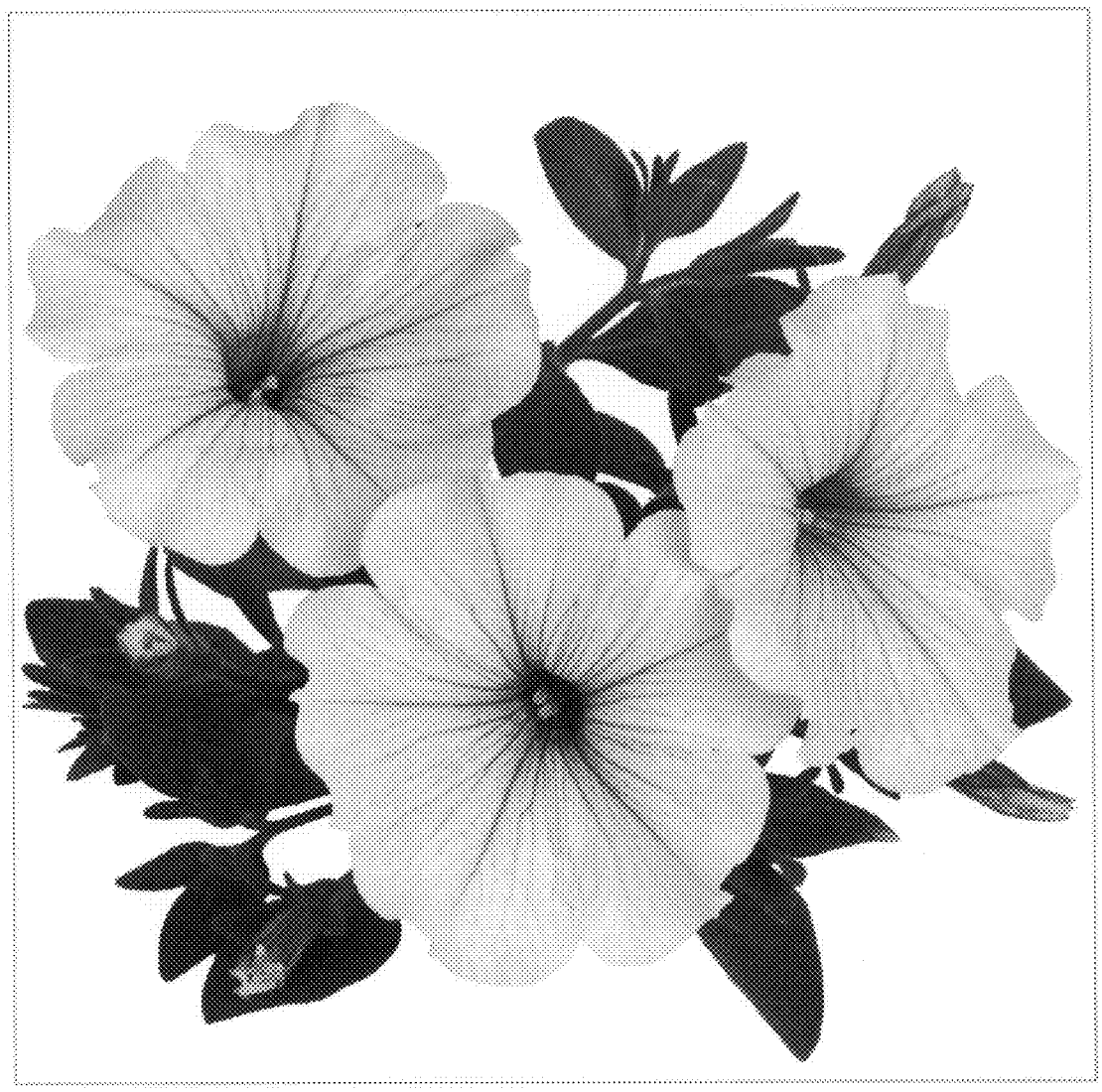

* * * * *